US00PP26865P3

(12) United States Plant Patent
Cho

(10) Patent No.: US PP26,865 P3
(45) Date of Patent: Jun. 21, 2016

(54) ***COLOCASIA* PLANT NAMED 'MORNING DEW'**

(50) Latin Name: *Colocasia esculenta*
Varietal Denomination: Morning Dew

(71) Applicant: John J. Cho, Paia, HI (US)

(72) Inventor: John J. Cho, Paia, HI (US)

( * ) Notice: Subject to any disclaimer, the term of this patent is extended or adjusted under 35 U.S.C. 154(b) by 134 days.

(21) Appl. No.: 13/999,753

(22) Filed: Mar. 19, 2014

(65) Prior Publication Data

US 2015/0271975 P1 Sep. 24, 2015

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Keith Robinson
(74) *Attorney, Agent, or Firm* — Barbara Campbell; Bethany R. Roahrig; Cochran Freund & Young, LLC

(57) ABSTRACT

A new cultivar of *Colocasia* plant named 'Morning Dew' that is characterized by large, glossy, sagittate leaves which are dark-green in color with golden and pale-green flecks; and the petioles of 'Morning Dew' exhibit contrasting light cream and dark-green or brown-black streaks, becoming light burgundy in color towards the point of attachment with the leaf, is disclosed.

3 Drawing Sheets

Figure 1:
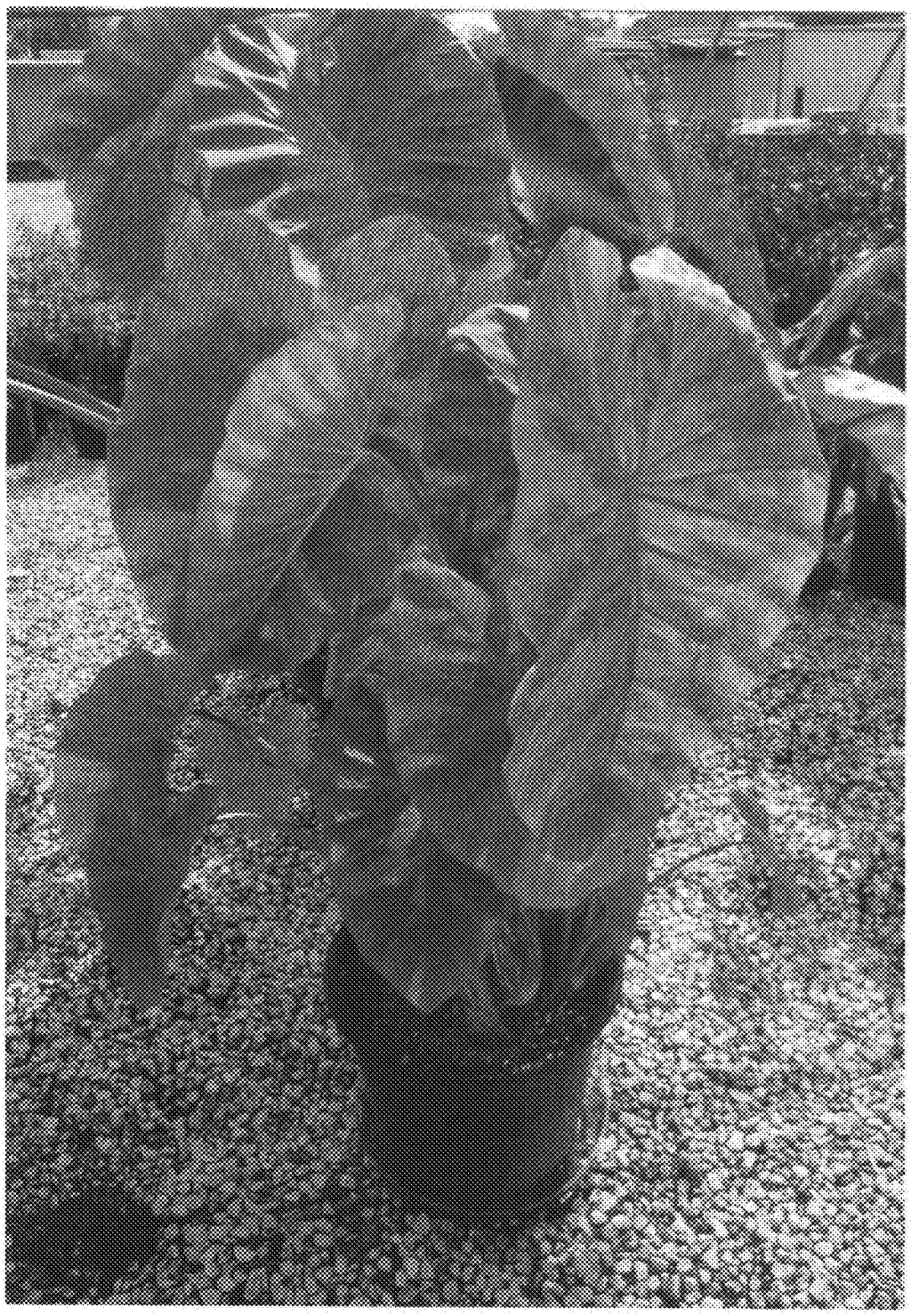

Genus and species: *Colocasia esculenta.*
Variety denomination: 'Morning Dew'.

BACKGROUND OF THE NEW PLANT

The present invention relates to a new and distinct variety of *Colocasia* commonly known as the taro plant or elephant ears. *Colocasia* is grown as a food crop or for use as an ornamental for container or the landscape. The new cultivar is known botanically as *Colocasia esculenta* and will be referred to hereinafter by the cultivar name 'Morning Dew'.

*Colocasia* is a tuberous rooted perennial which is native to tropical Asia and Polynesia. It grows to 1.5-2 m in height from starchy tubers. The leaves of *Colocasia* are heart-shaped and very large in size. The tuberous roots are cooked and eaten as a starchy staple in many tropical areas. *Colocasia* is also grown as ornamental plants for the landscape in warmer climates or as a container plant in colder areas.

The new *Colocasia* variety named 'Morning Dew' is the product of a formal breeding program carried out in Paia, Hi. The purpose of the breeding program is to develop new ornamental varieties with novel and striking ornamental characteristics, in particular leaves and stems. In addition, the selection of candidate varieties was made for strong clumping and basal branching habits in order to produce sturdy container plants for transportation and display.

'Morning Dew' is a seedling selection from the controlled pollination between the proprietary female parent '[203×6-2]8' (unpatented) and the proprietary male parent '2007A-1360' (unpatented). Initially designated as '2008-27', 'Morning Dew' was derived from a single plant selected in 2008.

The first asexual propagation of 'Morning Dew' was conducted in 2008 in Paia, Hi. by using huli propagation, whereby the apical shoots are separated from the plant by cutting the shoot at the top of the corm immediately above the newest leaf scar and planted. Evaluations in field and pot studies have shown that 'Morning Dew' reproduces true to type in successive generations of asexual propagation via huli propagation.

SUMMARY

The following traits have been repeatedly observed and represent the distinguishing characteristics of the new *Colocasia* variety named 'Morning Dew'. In combination these traits set 'Morning Dew' apart from all other varieties of *Colocasia* known to the inventor. 'Morning Dew' has not been tested under all possible conditions and phenotypic differences may be observed with variations in environmental, climatic and cultural conditions, however, without any variance in genotype:

1. 'Morning Dew' exhibits large, sagittate, dark-green leaves that are heavily speckled with golden and pale green flecks.
2. The surface of the leaves of 'Morning Dew' is glossy.
3. 'Morning Dew' exhibits a dense clumping habit.
4. The petioles of 'Morning Dew' exhibit pronounced longitudinal streaks which alternate in color between light cream and dark green or brown-black.
5. The petioles of 'Morning Dew' become light burgundy in color towards the point of attachment with the leaf (the piko).

DESCRIPTION OF THE PHOTOGRAPHS

The accompanying color photographs illustrate the overall appearance of 'Morning Dew' showing the colors as true as it is reasonably possible to obtain in colored reproductions of this type. Colors in the photographs may differ from the color values cited in the detailed botanical description, which accurately describe the actual colors of the new variety 'Morning Dew'. The photographs are of a plant grown from a planted huli after approximately 5 months and grown in 2-gallon containers outdoors, without any chemical growth regulator treatments in Oxnard, Calif.

FIG. 1 shows a whole plant view of 'Morning Dew'.

Figure 2:
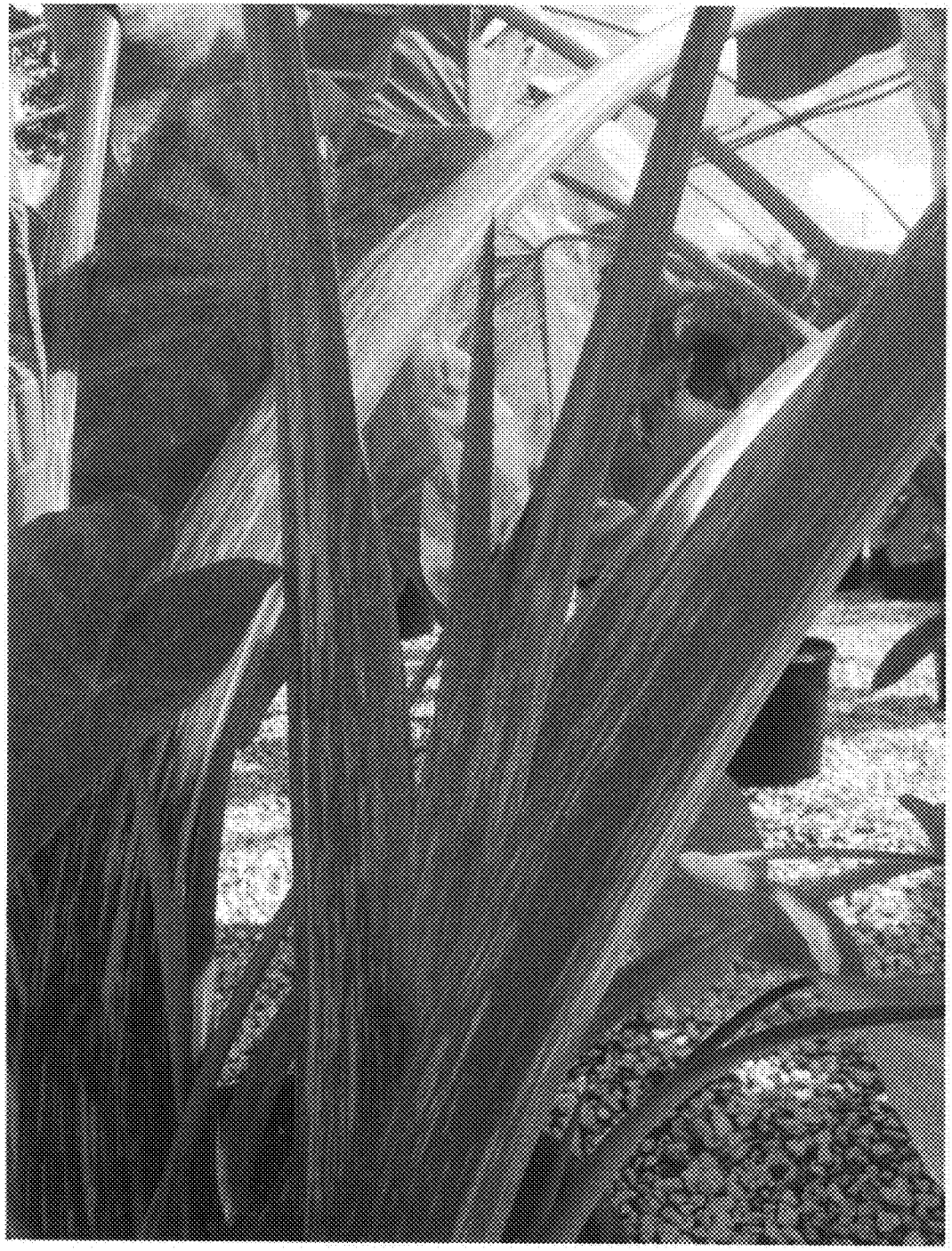

FIG. 2 shows the petioles of 'Morning Dew'. The petiole streaks are either light cream, or dark-green to brown-black. The dark-green and brown-black streaks coalesce and are dominant towards the base. As the petiole extends towards the leaf attachment (the piko) the white-yellow streaks become dominant, changing to light burgundy.

Figure 3:
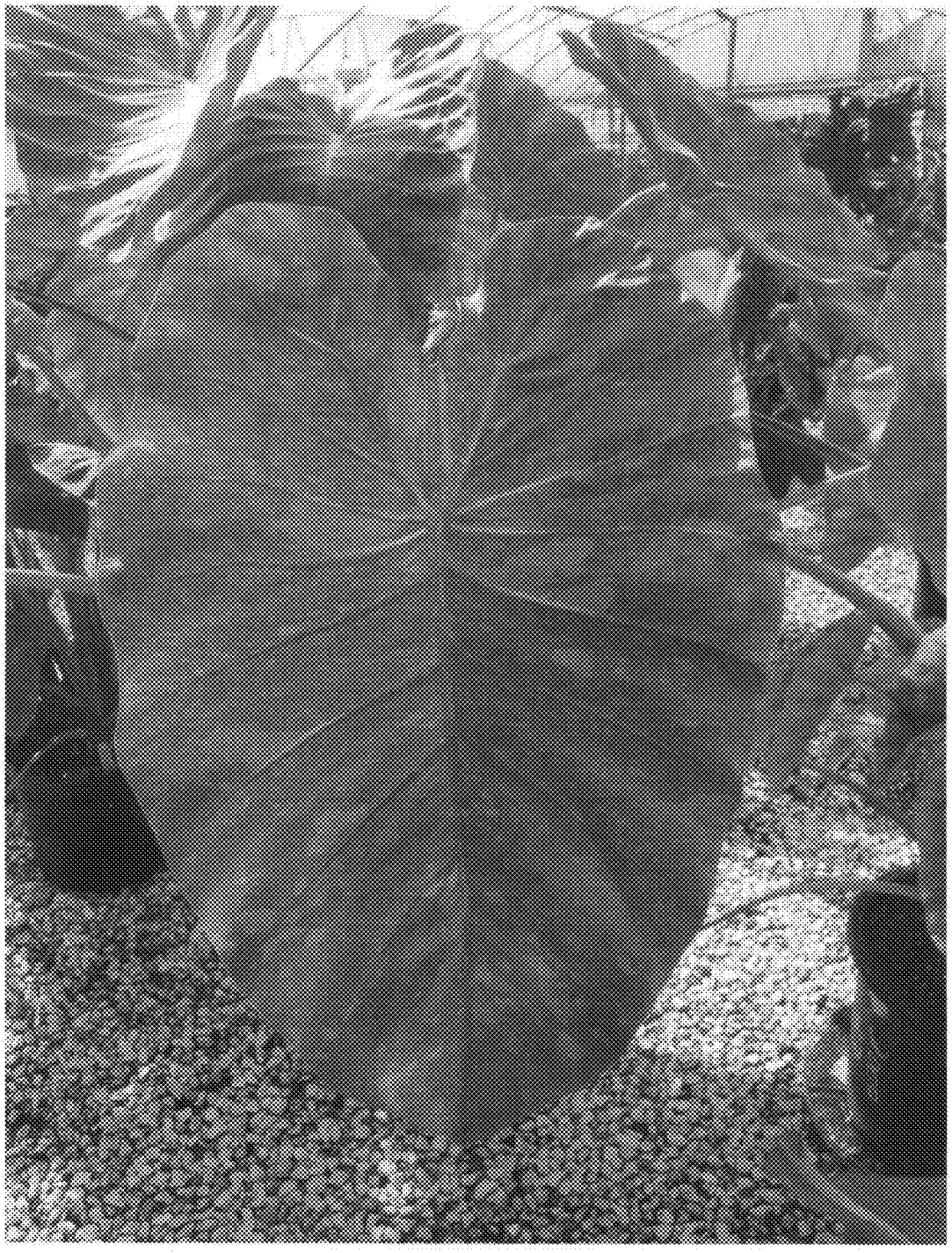

FIG. 3 illustrates the large glossy dark green sagittate leaf of 'Morning Dew' with its contrasting yellow-green and pale green flecking.

DESCRIPTION OF THE NEW VARIETY

The following is a detailed description of the new *Colocasia* plant named 'Morning Dew'. Data was collected from plants that were 3 to 6 months of age grown outdoors in the border soil in Santa Barbara, Calif. The color determinations are in accordance with The Fifth (2007) Edition of The Royal Horticultural Society Colour Chart, London, England, except where general color terms of ordinary dictionary significance are used. The growing requirements are similar to other *Colocasia*.

Classification:

*Genus and species.*—*Colocasia esculenta.*

*Denomination.*—'Morning Dew'.

*Common name.*—Taro or elephant ears.

Parentage:

*Female parent.*—'[203×6-2]8' (unpatented).

*Male parent.*—'2007A-1360' (unpatented).

Plant:

*Plant use.*—Food, container or landscape plant.

*Cultural requirements.*—Cultural requirements are well draining soil or growing media, full sun to partial shade.

*Root system.*—Fibrous.

*Root color.*—NN155C.

*Root development.*—At soil temperatures of 20 degrees C. to 25 degrees C., root initials are evident within 3 days; roots will reach edge of 1-gallon containers in 14 days.

*Plant vigor.*—Vigorous.

*Plant growth habit.*—Upright, non-spreading.

*Plant description.*—The plant has 4 to 6 suckers closely attached to the mother plant. A "mother plant" is the plant material which is first introduced into the soil to begin production. Typically, this plant material contains part of the huli and 2 to 3 leaf blades. This produces a "mother corm" which produces lateral shoots called "cormels" which give rise to daughter plants. Daughter plants begin to appear above soil level about 2 to 3 months after planting of the mother plant.

*Mother corm shape.*—Short cylindrical.

*Mother corn dimensions.*—2.0 cm to 3.0 cm in diameter and 1.0 cm in length.

*Number of cormels.*—3 to 5.

*Cormel (lateral shoot base) shape.*—Short cylindrical.

*Cormel dimensions.*—1.0 cm to 2.5 cm in diameter and 0.5 cm in length.

*Cormel attachment.*—Permanent if undisturbed; not readily detachable.

*Plant dimensions.*—Height, 65 cm to 75 cm; width, 85 cm to 1.0 m.

*Plant hardiness.*—USDA Zone 7b.

*Propagation.*—Propagation is accomplished by huli propagation and by tissue culture.

*Time to develop daughter plants.*—Appear above soil around 2 to 3 months after planting.

*Crop time (from a weaned tissue culture propagule).*—1.5 to 2.5 months.

Foliage:

*Petioles.*—Length: Up to 60 cm in length. Diameter: From 3.5 cm at base decreasing uniformly to 0.5 cm immediately below the piko attachment to the lamina. Strength: Strong. Color: Light cream, ranging between NN155A and 1D, with contrasting dark-green and brown-black streaks, ranging between 136B and 203A. The dark-green and brown-black streaks coalesce and are dominant towards the base. As the petiole extends towards the leaf attachment (piko) the light cream streaks become dominant, changing to light burgundy 182C and eventually coalescing into uniform 182C immediately below the piko. Surface texture: Glabrous and glossy. Sap color: Colorless.

*Leaf.*—Number: On average, a 5 to 6 month old plant produced from the mother corm maintains 5 functional leaves at a time; each new leaf is produced approximately every 10 days until the corm matures. Dimensions at maturity (5-6 months old): 40 cm in length and 25 cm in width. Average leaf sinus depth: 7.5 cm. Attitude: Oblique with reflexed apex. Shape: Sagittate. Margins: Entire, slightly undulating. Apex: Pointed. Base: Peltate. Attachment: Petiolate with characteristic tissue formed at junction of leaf blade with the upper termination of the petiole. This area of the leaf tissue is also known as the "piko" and is evident by virtue of its upper surface color being the same color as the veins or darker. The principal veins radiate from the piko. Piko color: 182C. Leaf sheath: Open, 2.0 cm in length where clasping the stem. Texture (both upper and lower surfaces): Glossy. Leaf color (both surfaces): Predominantly mid-green between 135A and 135B, with yellow-green flecks closest to N144B and pale green "patches" closest to 145C. Venation: Palmate. Veins: Three principal veins radiating from the piko with the largest a midrib extending from the piko to the tip of the lamina with up to 12 pairs of secondary veins radiating from it. Vein color (adaxial surface): 150D. Vein color (abaxial surface): 150C.

Inflorescence, flowers and reproductive organs: The inflorescence arises from the leaf axils. The inflorescence is made up of a short peduncle, a spadix, and spathe. The spadix is botanically a spike, with a fleshy central axis to which the small sessile flowers are attached. The spadix is 9.5 cm to 10 cm long, with female flowers at the base, male flowers towards the tip, and sterile flowers in between, in the region compressed by the neck of the spathe. The extreme tip or appendage of the spadix has no flowers at all. The spathe is a large yellowish bract, 19.5 cm to 21.5 cm long, which sheathes the spadix. The lower part of the spathe is light-green (150B) in color and wraps tightly around the spadix and completely occludes the female flowers from view. The top portion of the spathe is yellow (13C) in color and is rolled inward at the apex, but is open on one side to reveal the male flowers on the spadix. The top and bottom portions of the spadix are separated by a narrow neck region, corresponding to the region of the sterile flowers on the spadix.

*Peduncle*.—Shape: Cylindrical. Dimensions: Length is 35.0 cm and diameter is 1.0 cm. Strength: Strong, very stiff. Color: Light cream, ranging between NN155A and 1D, with dark brown longitudinal streaks, ranging between 136B and 203A. Surface texture: Glabrous and glossy.

Seed: Seed is not produced naturally since male and female flowers within each inflorescence do not mature at the same time. Pollination can be achieved manually or in nature, only with the presence of small insect pollinators which are found in regions of genetic origin of the species, and not Hawaii.

*Seed shape and dimensions*.—Ovate, length 1.3 mm, diameter 1.0 mm.

*Seed color*.—Straw yellow.

Disease and pest resistance/susceptibility: In common with *Colocasias* in general, 'Morning Dew' is susceptible to attack by *Tetranychus urticae*, commonly known as the red spider mite. Otherwise, the inventor has not observed that 'Morning Dew' is more or less susceptible to pests or diseases than other cultivars of the genus.

COMPARISON WITH PARENTAL LINES AND KNOWN VARIETY

Whereas 'Morning Dew' exhibits markedly variegated leaves and stems, the leaves and stems of both parents are uniformly colored. The male parent, '2007A-1360', exhibits uniformly light-green colored leaves with a glossy finish, with petioles which are uniformly light pink in color. The female parent, '[203×6-2]8' exhibits uniformly green leaves with a matte finish.

The closest comparison variety known to the inventor is *Colocasia* (unpatented), also listed as *Colocasia* 'Limeade'. Whereas 'Morning Dew' produces dark-green glossy leaves that are heavily speckled, the leaves of 'Lime-Aide' are matte and less prominently speckled with golden flecks. In addition, 'Morning Dew' produces secondary lateral shoots that are closely attached to the mother plant, forming a dense clump, as compared with 'Lime-Aide' which produces secondary lateral shoots on long stolons.

I claim:

1. A new and distinct variety of *Colocasia* plant named 'Morning Dew' as illustrated and described herein.

* * * * *